United States Patent
Yaesoubi et al.

(10) Patent No.: US 11,402,452 B2
(45) Date of Patent: Aug. 2, 2022

(54) SYSTEM AND METHODS FOR DYNAMIC COVARIANCE ESTIMATION OF A MULTIVARIATE SIGNAL

(71) Applicant: STC.UNM, Albuquerque, NM (US)

(72) Inventors: Maziar Yaesoubi, Albuquerque, NM (US); Vince Calhoun, Albuquerque, NM (US)

( * ) Notice: Subject to any disclaimer, the term of this patent is extended or adjusted under 35 U.S.C. 154(b) by 925 days.

(21) Appl. No.: 16/198,446

(22) Filed: Nov. 21, 2018

(65) Prior Publication Data

US 2019/0154779 A1 May 23, 2019

Related U.S. Application Data

(60) Provisional application No. 62/589,279, filed on Nov. 21, 2017.

(51) Int. Cl.
| | | |
|---|---|---|
| *G01R 33/54* | (2006.01) | |
| *G01R 33/56* | (2006.01) | |
| *A61B 5/245* | (2021.01) | |
| *A61B 5/369* | (2021.01) | |

(52) U.S. Cl.
CPC ......... *G01R 33/54* (2013.01); *G01R 33/5608* (2013.01); *A61B 5/245* (2021.01); *A61B 5/369* (2021.01)

(58) Field of Classification Search
USPC .......................................................... 702/19
See application file for complete search history.

(56) References Cited

U.S. PATENT DOCUMENTS

2016/0242690 A1* 8/2016 Principe ................... A61B 5/16

OTHER PUBLICATIONS

Aharon, M., et al., "K-SVD: An Algorithm for Designing Overcomplete Dictionaries for Sparse Representation", IEEE Transactions on signal processing, Nov. 2006, 4311-4322.
Allen, E.A., et al., "Tracking Whole-Brain Connectivity Dynamics in the Resting State", Cereb Cortex, Mar. 2014, 24, 663-676.
Allen, E.A., et al., "A baseline for the multivariate comparison of resting-state networks", Front System Neuroscience, Feb. 2011, 5, 2.
Battaglia, D., Thomas, "Functional Connectivity Dynamics of the Resting State across the Human Adult Lifespan", bioRxiv, Feb. 2017.
Calhoun, V.D., et al., "Multisubject independent component analysis of fMRI: a decade of intrinsic networks, default mode, and neurodiagnostic discovery", 2012, IEEE Rev Biomed Eng 5, 60-73.
Calhoun, V.D., et al., "A method for making group inferences from functional MRI data using independent component analysis", 2001, Human Brain Mapping 14, 140-151.

(Continued)

*Primary Examiner* — Rodney E Fuller
(74) *Attorney, Agent, or Firm* — Valauskas Corder LLC

(57) ABSTRACT

A system and methods of capturing rapid changes in complex systems by examining the interaction of the various components within the system. A multivariate signal is decomposed into a dictionary of elements and a corresponding sparse mixing matrix Each dictionary element may provide a rank-1 estimation of a disjoint partition of time points of the signal that may permit estimation of the covariance of each partition using an outer-product of the corresponding dictionary element.

7 Claims, 11 Drawing Sheets

(56) References Cited

OTHER PUBLICATIONS

Chang, C., et al., 2010. "Time-frequency dynamics of resting-state brain connectivity measured with fMRI". Neuroimage 50, 81-98.
Chen, J.E., et al., 2015. "BOLD fractional contribution to resting-state functional connectivity above 0.1 Hz". Neuroimage 107, 207-218.
Chen, J.E., et al., 2017. "Nuisance Regression of High-Frequency Functional Magnetic Resonance Imaging Data: Denoising can be Noisy". Brain Connect.
Eavani, H., et al., 2013. Unsupervised learning of functional network dynamics in resting state fMRI. Inf Process Med Imaging 23, 426-437.
Erhardt, E.B., et al., 2011. Comparison of Multi-Subject ICA Methods for Analysis of fMRI Data. Human Brain Mapping 32, 2075-2095.
Ferri, C.P., et al., Alzheimer's Disease, I., 2005. "Global prevalence of dementia: a Delphi consensus study". Lancet 366, 2112-2117.
Friston, K.J., et al., 1997. "Psychophysiological and modulatory interactions in neuroimaging". Neuroimage 6, 218-229.
Handwerker, D.A., et al., 2012. "Periodic changes in fMRI connectivity". Neuroimage 63, 1712-1719.
Hutchison, R.M., et al., 2013. "Dynamic functional connectivity: promise, issues, and interpretations". Neuroimage 80, 360-378.
Kaiser, R.H., et al., 2016. "Dynamic Resting-State Functional Connectivity in Major Depression". Neuropsychopharmacology 41, 1822-1830.
Kim, J., et al., 2008. "Investigating the neural basis for fMRI-based functional connectivity in a blocked design: application to interregional correlations and psycho-physiological interactions". Magn Reson Imaging 26, 583-593.

Liu, X., et al., 2013. "Time-varying functional network information extracted from brief instances of spontaneous brain activity". Proceedings of the National Academy of Sciences of the United States of America 110, 4392-4397.
Ma, S., et al., 2011. "Automatic identification of functional clusters in FMRI data using spatial dependence". IEEE Trans Biomed Eng 58, 3406-3417.
Rashid, B., et al., 2014. "Dynamic Connectivity States Estimated from Resting fMRI Identify Differences among Schizophrenia, Bipolar Disorder, and Healthy Control Subjects". Frontiers in Human Neuroscience 8.
Service, S.K., et al., 2014. "Re-sequencing Expands Our Understanding of the Phenotypic Impact of Variants at GWAS Loci". Plos Genetics 10.
Shakil, S., et al., 2016. "Evaluation of sliding window correlation performance for characterizing dynamic functional connectivity and brain states". Neuroimage 133, 111-128.
Trapp, C., et al., 2017. "On the detection of high frequency correlations in resting state fMRI". Neuroimage.
Yaesoubi, M., et al., 2015. "Dynamic coherence analysis of resting fMRI data to jointly capture state-based phase, frequency, and time-domain information". Neuroimage 120, 133-142.
Yaesoubi, M., et al., 2015. "Mutually temporally independent connectivity patterns: A new framework to study the dynamics of brain connectivity at rest with application to explain group difference based on gender". Neuroimage 107, 85-94.
Calhoun, Vince D., et al., "The Chronnectome: Time-Varying Connectivity Networks as the Next Frontier in fMRI Data Discovery". Neuron, 2014. 84(2): p. 262-274.
Leonardi, N., et al., Principal components of functional connectivity: a new approach to study dynamic brain connectivity during rest. Neuroimage, 2013. 83: p. 937-50.

* cited by examiner

State 1     State 2     State 3     State 4     State 5

SYSTEM AND METHODS FOR DYNAMIC COVARIANCE ESTIMATION OF A MULTIVARIATE SIGNAL

CROSS-REFERENCE TO RELATED APPLICATIONS

This application claims the benefit of U.S. Provisional Patent Application No. 62/589,279 filed Nov. 21, 2017, incorporated by reference.

STATEMENT REGARDING FEDERALLY SPONSORED RESEARCH

This invention was made with government support under grant no. 1539067 awarded by the National Science Foundation, and grant nos. EB020407 and EB006841, and GM103472 awarded by the National Institutes of Health. The government has certain rights in the invention.

FIELD OF INVENTION

The present invention relates generally to processing a multivariate signal. More specifically, the invention is directed to measuring dynamic connectivity between components in a system having variable rates of change without local assumption.

BACKGROUND OF THE INVENTION

Coherent spatially-distributed fluctuations as a vehicle to measure the functional integration of the brain have been investigated under various cognitive states and may be commonly referred to as functional connectivity ("FC"). In task-based studies of FC, underlying cognitive states are hypothesized to constitute a task-focused state and a short period of resting-state as the baseline. Neurophysiological interpretations are typically driven by context-dependent connectivity analysis based on these states of the brain as in psycho-physiological interaction (PPI).

Task-free studies—referred to as resting-state (RS) studies—have challenged previous assumptions that a resting-state represents only a singleton baseline cognitive state and suggest also the occurrence of dynamic functional connectivity during an extended resting-state session. Problematically, compared to task-based studies, there is a lack of prior knowledge of such expected dynamics during the resting state due to the lack of designed or explicit stimuli of the brain. Overcoming this problem may require leveraging approaches that capture dynamics of the connectivity without the need for prior knowledge of when changes of the underlying states may occur, although each approach includes some assumption regarding the underlying nature of dynamics. For example, a commonly used approach of measuring connectivity based on the selection of a sliding-window assumes that connectivity at a given timepoint (usually at the center of the window) may be estimated from all the samples of the input time series spanned by the selected window. This is commonly referred to as a temporal locality assumption. Moreover, connectivity may be estimated by measuring the correlation or covariance between samples in a given window if it is assumed that the samples are derived from a multivariate Gaussian distribution.

The validity of these assumptions depends on the actual nature of the time series. For example, a locality assumption is justified in a time series in which the known rate of change is much slower than the data sampling rate. Likewise, a Gaussian assumption—based on the central limit theorem—may be justified when each timepoint in the time-series measures the average of many independent and identically distributed (I.I.D.) samples from an unknown distribution.

Although these assumptions may be validated in many types of time series, such as in financial data, working with brain functionality data may be less certain due to the unknowns regarding the actual nature of the captured signal of the brain. Compounding this issue is the variety of modalities that capture different correlates of true neurophysiological activity of the brain with different spatial and temporal resolution. For example, in the case of Functional Magnetic Resonance Imaging (fMRI)—which may measure blood flow or oxygen levels in the brain,—voxel time series commonly have been modeled as the convolution of neurological activity with a slow-varying hemodynamic response function (HRF) in which a locality assumption may be justified.

Nevertheless, recent studies have found evidence of changes in both activation of and connectivity between voxels and networks (groups of functionally related voxels) at a rate beyond what has been often assumed. In terms of frequency, the blood-oxygen-level dependent signal, as a reflection of the underlying neurological activity and the connectivity due to it, has been assumed to span the range between 0.01 and 0.1 Hz, and may agree with the commonly used models of HRFs. However, other studies suggest the occurrence of observable activity and connectivity in higher frequencies up to the maximum observable frequency. Since such studies are very recent, there have been various speculations on the sources of observed high-frequency activation and connectivity variance. These speculations include the relationship between nuisance variables due to improper models of controlling for these variables and also questioning conventional models for Blood Oxygen Level Dependent (BOLD) fMRI signal generation that are unable to explain these observations. Thus, these studies question the validity of assumptions commonly used in fMRI analysis, including the locality assumption, and support the use of models that may at least capture information that may be blurred out or ignored by existing models.

Various alternative approaches have been proposed to relax the limiting assumption of locality. These include adaptive windowing based on the current temporal frequency of the data by leveraging time-frequency analysis and measuring dependence in the augmented domain. Other approaches do not require an explicit selection of a window but may still have an inherited locality assumption. These include approaches based on filtering in time such as Hidden Markov Models (HMMs). And although HMM may be implemented in a way that does not require a windowing operation, the traditional HMM still includes an embedded locality assumption in the transition probability between states that may be stationary in time. Thus, like other methods that employ a local assumption, HMM remains unable to measure rapid changes in connectivity such as at single time points.

Accordingly, there is a need for a system and methods of estimating the covariance of a multivariate signal without local assumptions that may permit the measurements of rapid changes in a complex system. The present invention satisfies this need.

SUMMARY OF THE INVENTION

The present invention is directed to a system and methods of capturing rapid changes in the overall state of highly complex systems based upon examining the connectivity—that is, the interaction—of the various independent components comprising the system. For example, such a system and methods of may be useful in analyzing the dynamic changes that occur in the finance sector by detecting fluctuations in the stock market or economy, analyzing and predicting weather patterns, analyzing data to track current geopolitical climate, analyzing geographic crime data to determine changes in overall crime patterns, and detecting changes in biological systems through the use of imaging and diagnostic devices.

One certain embodiment of the invention may permit the capture of a dynamic covariance of a multivariate signal from a complex system that may include the steps of providing a dictionary of elements, receiving an input multivariate signal, decomposing the input signal into a dictionary and a sparse mixing matrix, representing the input multivariate signal as a plurality of data points such that each data point may be represented by a singleton dictionary element, and estimating the dynamic covariance of a partition of data-points using a self-outer product such that the self-outer product corresponds to the singleton dictionary element up to a scaling value.

Advantageously, certain embodiments of the invention may be used to capture dynamic connectivity of functional fMRI networks that does not require either explicit or implicit locality assumption. Use of such embodiments may permit the observation of changes in the connectivity of the brain that—although occurring close in time—may belong to different underlying sources of activity. Further, these observation of changes in connectivity with heterogeneous rates may approach the Nyquist rate, that is, the rate at which a signal may be sampled without introducing errors. In other words, the observable changes may occur on the scale of one timepoint and may identify connectivity with similar modularity and novel connectivity patterns previously undetectable using known methods.

Advantageously, the method according to certain embodiments of the invention may be applied to any multivariate signal such as a signal from other imaging modalities including an electroencephalogram and a magnetoencephalogram that may have a higher sampling rate than fMRI to permit capture of more spontaneous dynamic connectivity. Further, the use of certain embodiments of the invention may be used also in task-based studies such as auditory oddball task fMRI data.

Advantageously, the estimation of covariance may be the equivalent of finding the dominant linear pattern—that is, the rank-1 estimation—in the sample space without using information about the time domain.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF THE INVENTION

The present invention is directed to a system and methods of capturing small changes in complex system by analyzing the interactions of various components within the system. In particular, embodiments of the invention may detect quick changes that may have been undetectable by prior art methods by capturing the dynamic covariance of a multivariate signal without local assumptions that may include leveraging a sparse dictionary decomposition of the input signal of network time courses.

Generally, certain preferred embodiments of the invention may use an input multivariate signal, that is, an n-dimensional multivariate signal that may be represented a two-dimensional matrix where each column in the matrix represents n-dimensional time points of the signal. The signal may be decomposed into a matrix of a finite number of n-dimensional dictionary elements and a corresponding mixing matrix based on a major constraint that each time point of the input signal is represented by only one scaled dictionary element. The scaling factor may be derived from the mixing matrix. The decomposition of the signal with the given major constraint may be achieved, for example, through the use of the K-SVD algorithm (Aharon et al., 2006. *K-SVD: An Algorithm for Designing Overcomplete Dictionaries for Sparse Representation.* IEEE Transactions on signal processing 54, 4311-4322) according to the following: $X \cong D \times M$ s.t. $\forall i \|M_i\|_0 = 1$. Following the decomposition of the signal, each element of the dictionary may permit a rank-1 estimation of a disjoint partition of time point of the signal. Then, using the rank-1 estimation of the partition, the covariance of each partition may be estimated with an outer product of the corresponding dictionary element.

For purposes of this application, the present invention may be discussed in reference to detecting functional connectivity of the brain using fMRI data, but the discussion is merely exemplary. The present invention may be used to capture extremely quick changes in the state of any highly complex systems that may include, but is not limited to, changes in the stock market or economy, changes in brain connectivity using medical devices (e.g., fMRI, MEG, EEG, etc.), predicting weather patterns, geopolitical forecasting and analysis, social network analysis, and crime prediction and analysis.

Figure 2:
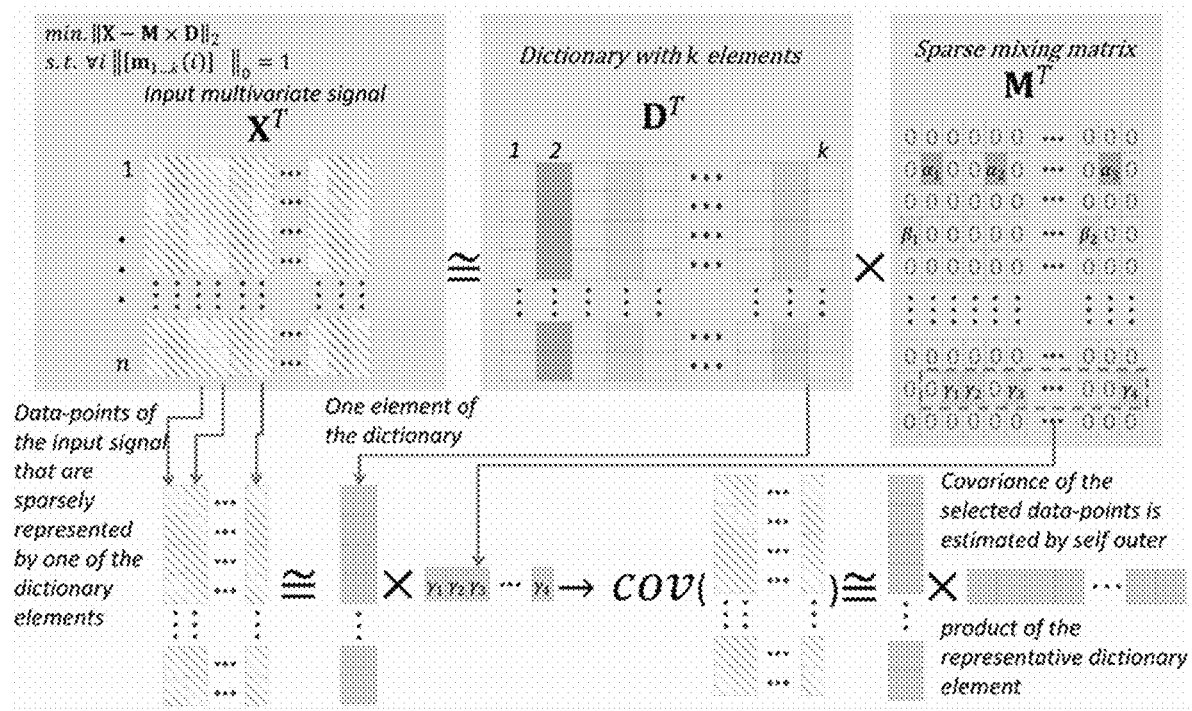
FIG. 2 illustrates one certain embodiment of the proposed method of the invention. By using a K-SVD algorithm, an input multivariate signal may be decomposed into a dictionary and a sparse mixing matrix. Based on a sparsity constraint of $\|M_i\|_0 = 1$, a singleton dictionary element may represent each data-point. Covariance of a partition of data-points may be estimated with a self-outer product of the corresponding dictionary element up to a scaling value.

FIG. 2 and FIG. 3 illustrate one certain preferred embodiment of a system and methods of capturing the dynamic functional connectivity of functional networks, such as one or more fMRI networks. Initially, it is assumed an n-dimensional input signal may be defined as $X(t)=[x_1(t), x_2(t), \ldots, x_n(t)] \in \mathbb{R}^{T \times n}$. Each feature vector $x_i$ (columns of $X(t)$) consists of I.I.D. samples and since the focus may be primarily or only on the estimation of covariance/correlation as the measure of dependence, there may be an inherent assumption that the data samples have a Gaussian distribution where the uppercase bold letter (e.g. X(t)) represents a matrix (and if indexed by t, it represents a multivariate signal, i.e., realization from a random process), lowercase bold letter indexed (e.g. v) represents a (column) vector (and similarly if indexed by t, it represents a univariate signal again a realization of a random process), and an Italic letter (e.g. k or K) represents a scalar variable. We are also assuming all the feature vectors have zero mean. X(t) is low-rank and may be reasonably (i.e., with small residual error) approximated it with its rank-1 estimate:

$$X(t) \cong m(t) v^T \qquad \text{Eq. (1)}$$

And since the covariance between any two feature vectors of X(t) (e.g. $x_i(t)$, $x_j(t)$) is equal to $E(x_i(t)x_j(t))-E(x_i(t))E(x_j(t))$ and becomes equal to $E(x_i(t)x_j(t))$ since $E(x_i(t))=E(x_j(t))=0$, $\text{cov}(x_i(t), x_j(t))$ may be also approximated by:

$$\text{cov}(x_i(t), x_j(t))$$
$$\cong \text{var}(m(t)) v_i v_j \qquad \text{Eq. (2)}$$

where $v_i$ and $v_j$ are $i^{th}$ and $j^{th}$ elements of the vector v.

The above equation then may be extended to the approximation of the covariance of the whole input matrix X(t) as follows:

$$\text{cov}(X(t)) = \begin{bmatrix} \text{cov}(x_1(t), x_1(t)) & \cdots & \text{cov}(x_n(t), x_1(t)) \\ \vdots & \ddots & \vdots \\ \text{cov}(x_1(t), x_n(t)) & \cdots & \text{cov}(x_n(t), x_n(t)) \end{bmatrix} \qquad \text{Eq.(3)}$$

$$\cong \text{var}(m(t)) \begin{bmatrix} v_1^2 & \cdots & v_n v_1 \\ \vdots & \ddots & \vdots \\ v_1 v_n & \cdots & v_n^2 \end{bmatrix}$$

$$= \text{var}(m(t)) \, v \, v^T$$

where var(m(t)) is a constant scalar and—when ignored—allows for the estimation of cov(X(t)) by a common matrix operation such as a simple self-outer-product of vector v up to a scaling ambiguity.

As is evident from the above equations, the estimation of covariance may be the equivalent to finding the dominant linear pattern (rank-1 estimation) in the sample space (without using the information about the time domain). For example, in a sliding-window analysis, a goal may be to find such linear pattern in the space of samples that lie in the window and a different linear pattern is fitted to each window. This is similar conceptually to piecewise linear regression although in the above instance, the focus may be on the estimation of covariance such that a different kind of linear pattern may be fitted which may not conform to the locality assumptions included in previous methods.

Figure 1A:
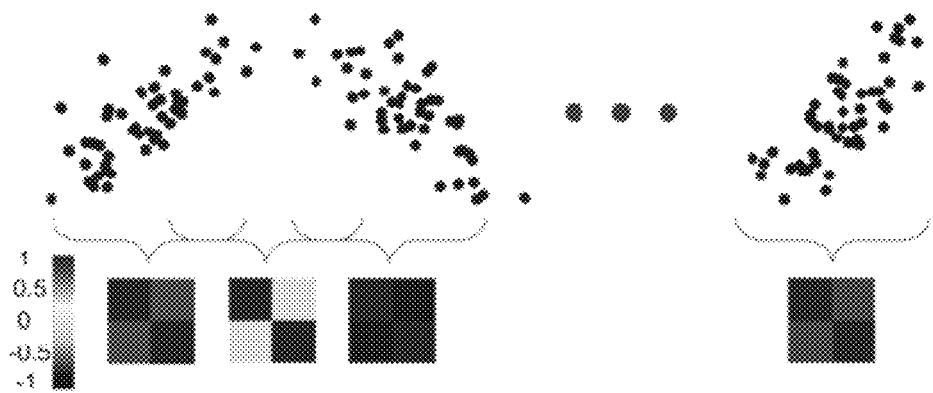
FIG. 1A illustrates a simulated 2-D signal including data samples driven from two Gaussian distributions with a different covariance matrix at each period (50 sample-points here). A correct choice of sliding window may capture underlying dynamic covariance matrices if the samples fit the locality assumption but also may generate spurious results if the samples do not confirm to the embedded assumption.
Figure 1B:
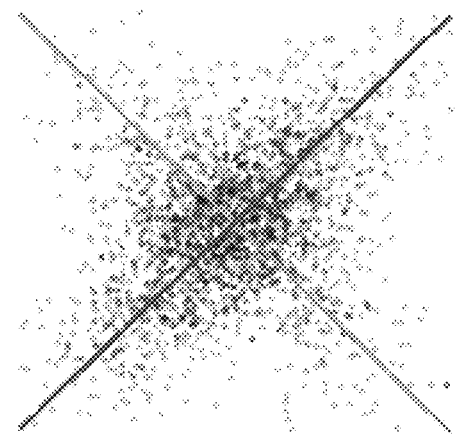
FIG. 1B illustrates the removal of time information from signal data-points to study the signal in the sample space such that dynamic covariance matrices would map to the dominant linear patterns in this space.

Dynamic covariance translates into having multiple linear patterns in the sample space, each of which includes an estimated covariance of the disjoint subset of samples. FIG. 1A and FIG. 1B further describes this concept. Here, a two-dimensional (2-D) signal may be simulated that includes samples driven from two Gaussian distributions with a different covariance matrix at each period (50 sample-points here). As illustrated in FIG. 1A, typically, a sliding-window analysis may be used to capture the true underlying dynamic covariance matrices. However, the sliding-window analysis may include also an inaccurate estimation at some periods when samples from different distributions lay in the same window. These inaccuracies may be exacerbated by choosing an incorrect window size.

FIG. 1B illustrates the simulated dynamic covariance matrices mapped to the linear patterns in the sample space according to one embodiment of the invention. The sparse dictionary representation of the same sample space may permit an estimate of the dominant linear patterns which—as discussed above—translate to the underlying dynamic covariance matrices.

The data samples may then be partitioned such that, after computing a rank-1 estimation for each partition separately, the sum of the residuals between the data sample values and their corresponding rank-1 estimations may be minimized. It is noted that no assumptions of the sizes of the partitions and/or assigning a sample to a partition provides any information on the assignment of other samples in the partition; rather, it is only the number of partitions that should be pre-selected.

Next, the disjoint partitions $s_1, s_2 \ldots, s_k$ (each $s_i$ is a set of sample indices) are found in order to minimize the following:

$$\sum_{i=1}^{k} C_i \qquad \text{Eq.(4)}$$

where $C_i = \|X(t) - m(t) v_i^T\|_2$ and $t \in s_i$

As is shown, the above optimization problem is non-convex without additional constraints. However, posing the problem as a sparse dictionary learning problem may permit an accurate approximation to the solution for the partitioning problem as follows: a number of dictionary elements k are learned such that each sample in the sample space is approximated by one and only one (this is where the sparse representation constraint plays a role) dictionary element. The dictionary elements may be the equivalent of vectors $v_{s_i}$ in equation 4.

The sparse dictionary learning algorithm aims to sparsely represent input matrix X(t) with dictionary $D \in \mathbb{R}^{k \times n}$ and mixing matrix $M(t)=[m_1(t), m_2(t), \ldots, m_k(t)] \in \mathbb{R}^{T \times k}$ where k is the number of dictionary elements. Sparse representation means that each row of X(t) (i.e. each sample) is a sparse linear combination of dictionary D meaning rows of mixing matrix M(t) is sparse. A general formulation of sparse dictionary learning is as follows:

$$\min_{D,M} \|X(t) - M(t)D\|_2 + \lambda \sum_i \|[m_{1\ldots k}(i)]\|_0 \qquad \text{Eq.(5)}$$

Where $m_{1\ldots k}(i)$ is the $i^{th}$ row of mixing matrix M and $\lambda$ is a regularizer parameter that controls degree of sparsity of the solution.

For this purpose—since only a rank-1 estimation of the samples is evaluated—the sparsity constraint in the above formula should be changed to a mathematical constraint of $\forall i \|m_{1\ldots k}(i)\|_0 = 1$. This may be achieved through the use of the K-SVD algorithm. The K-SVD method differs from the above formulations in that the sparsity constraint on the mixing matrix is a hard constraint. The sparsity level may be set to any integer value which in our case we choose as 1. This means that each column of mixing matrix M(t) has one and only one non-zero value which corresponds to our desired rank-1 estimation of the samples which mean the formulation of K-SVD algorithm would now be as follows:

$$\min_{D,M(t)} \|X(t) - M(t)D\|_2 \text{ s.t. } \forall i \|m_{1\ldots k}(i)\|_0 = 1 \qquad \text{Eq.(6)}$$

Similar to equation Eq. (5), the above formulation may be also non-convex but K-SVD may approximate the desired solution by finding a solution which is in fact a local minimum. The K-SVD algorithm iterates between first fixing D (for the first iteration D is randomly selected from the input data) and solving the equation for M(t) and this process may be reversed in the next iteration. In order to ensure the solution proposed by K-SVD is in fact a good approximation of the desired solution, an K-SVD algorithm may be applied to the same data but with different initializations of D for multiple iterations and select the solution with the minimum residual (equation Eq. (4)).

Certain embodiments of the present invention may be used to investigate the dynamic connectivity states between functional networks of the brain using rs-MRI imaging. Functional networks of the brain may be defined with either prior anatomical and functional knowledge of the brain, which are then used to define regions of interests (ROIs) as the functional networks, or in a more flexible approach, these networks can be retrieved using a data-driven approach with no prior knowledge as in independent component analysis (ICA). Embodiments of the present invention may utilize the latter to permit capture of subject-specific networks while simultaneously allowing variation of a given network between subjects.

Figure 3A:
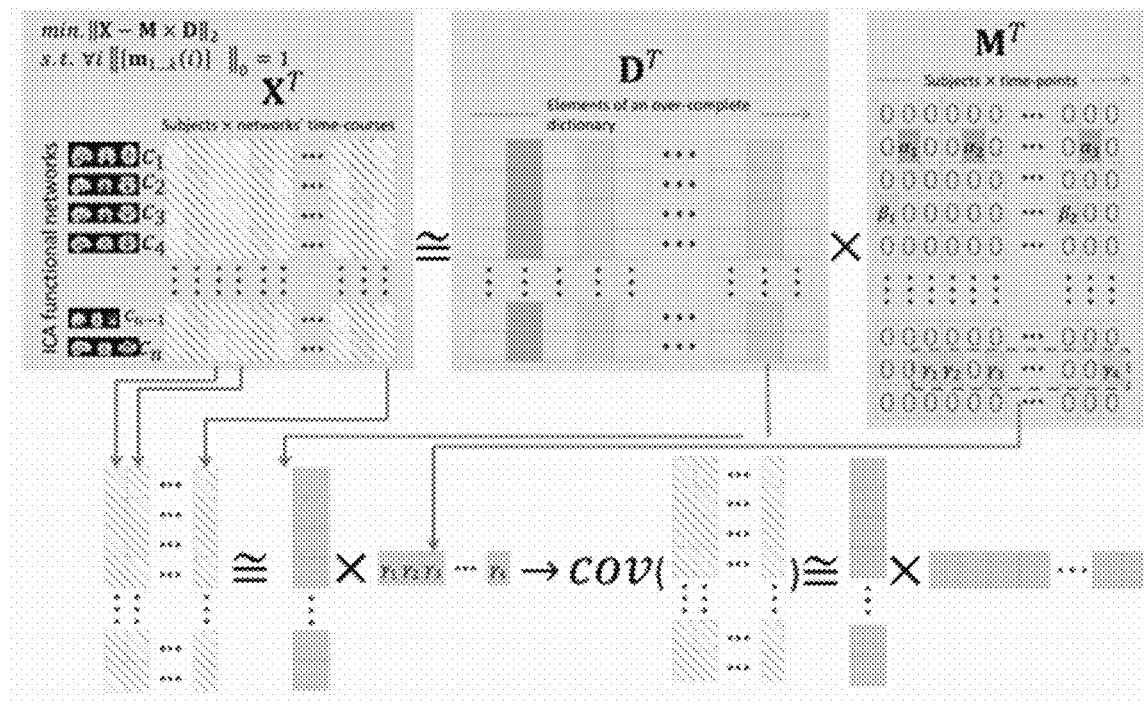
FIG. 3A illustrates an application of one embodiment of the invention to resting-state (rs) fMRI data. After decomposing the rs-fMRI data into functional networks and the corresponding time-courses, subject-wise time-courses of all subjects are concatenated along time to form an input multivariate signal. Each row of the input signal corresponds to each network's time-courses of multiple subjects. This input signal may be then decomposed into a dictionary with a number of elements (e.g., 5 dictionary elements) as well as a corresponding sparse mixing matrix.
Figure 3B:
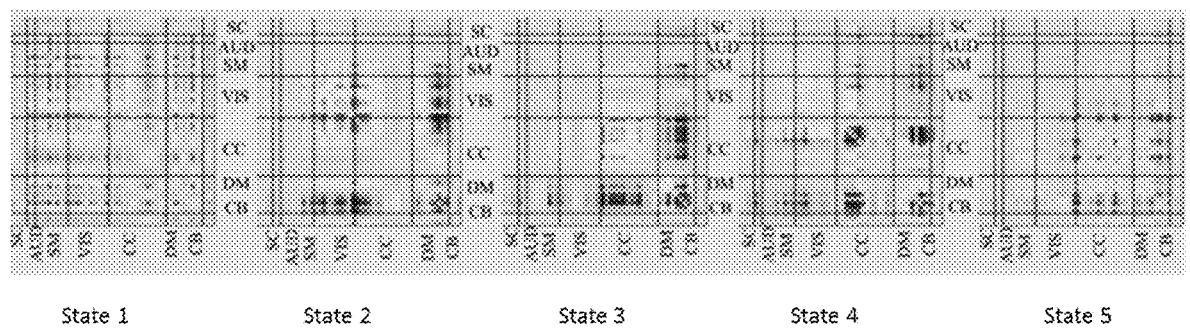
FIG. 3B illustrates a self-outer product of each dictionary element corresponds to one of the dynamic connectivities of the multi-subject rs-fMRI.

As illustrated in FIG. 3A, rs-MRI data initially may be decomposed into functional networks and corresponding time courses from each subject and concatenated along time to form the input multivariate signal. The multivariate signal may then be decomposed into a dictionary of elements and a corresponding sparse mixing matrix according to, for example, equations 1-6. The number of dictionary elements may be estimated or selected based on prior knowledge of the problem to be solved or according to other methods known in the art. In certain embodiments of the invention, the multivariate signal may be decomposed into one or more dictionary elements, and preferably 3 to 7 dictionary elements, and more preferably, 5 dictionary elements. FIG. 3B illustrates the stated covariance of the multivariate signal through a self-outer product of the dictionary elements that may represent the connectivity between different dimensions of the multivariate signal corresponding to different regions of the brain.

In order to measure the dynamic connectivity states between functional networks of the brain, resting-state scans of 405 healthy subjects—of which 200 are female—that range in age from 12 to 35 years with the mean age of 21 years were collected using a single fMRI scanner device (3-T Siemens Trio with a 12-channel radio frequency coil and it was used to acquire $T_2$*-weighted functional images using a gradient-echo EPI sequence with TE=29 ms, TR=2 s, flip angle=75°, slice thickness=3.5 mm and gap=1.05 mm, FOV=240 mm, matrix size=64×64, voxel size=3.75 mm×3.75 mm×4.55 mm). Subjects—with eyes open—were instructed to fixate on a foveally presented cross. After the scan, the first four image volumes were removed to avoid T1 equilibration effects followed by realignment, slice-timing correction, spatial normalization, reslicing to 3×3×3 mm³ voxels, and spatial Gaussian smoothing (FWHM=5 mm).

Figure 8:
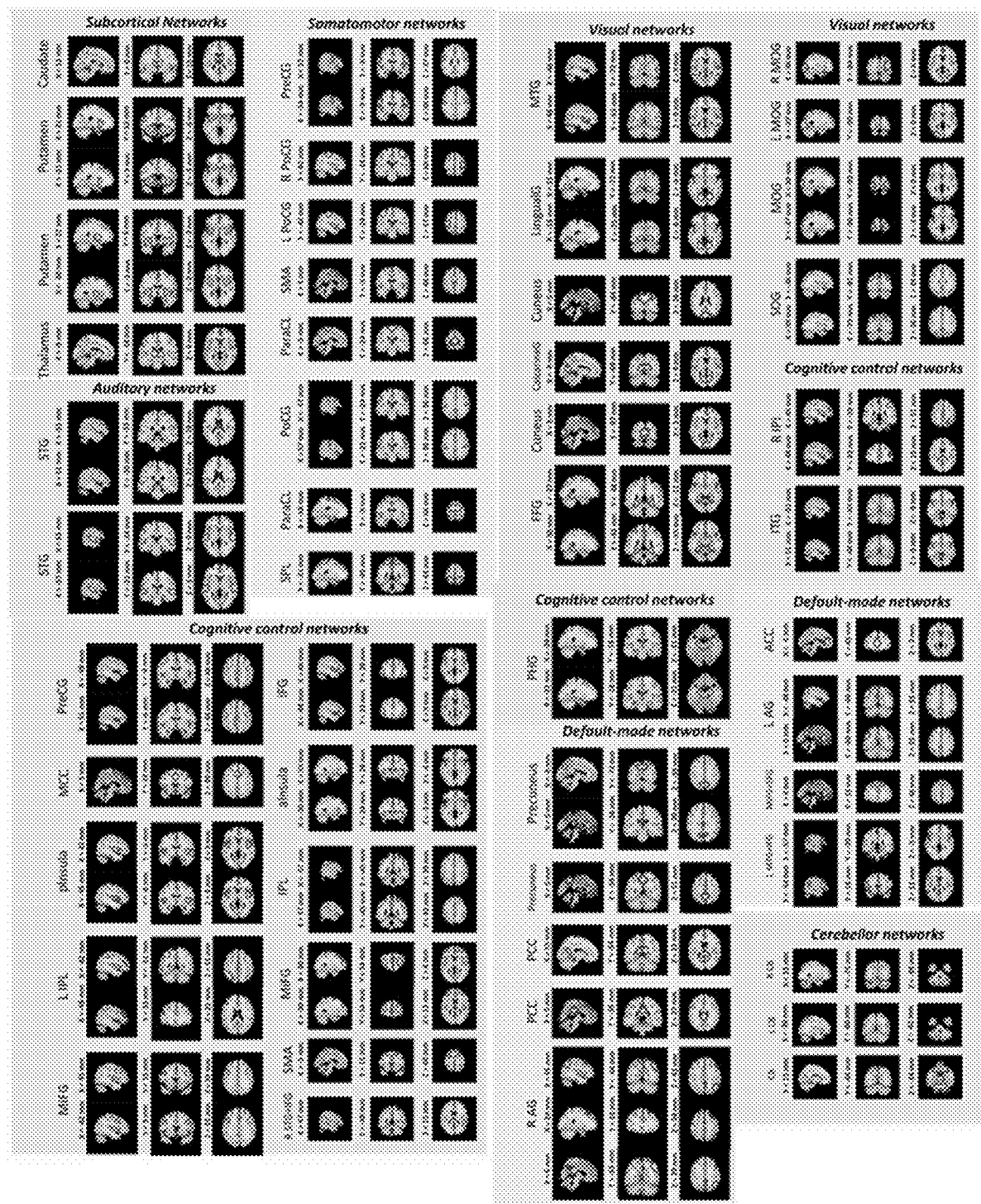
FIG. 8 illustrates a visual representation of ICA components identified as functional resting-state networks of the brain. The sagittal, coronal and axial slices along with its peek coordinate are shown for each network.

Next, implementation of group spatial ICA (gsICA) in the GIFT toolbox (http://mialab.mrn.org/software/gift) was used to acquire 100 functional networks that may be represented by ICA components according to the following: first, principal component analysis (PCA) may be performed separately for each subject to find 120 principal components in the voxel-space of each subject. These principal components may be then concatenated along time for all subjects and another PCA may be performed on this concatenated data to find 100 "group" PCs. Next, ICA may be used to identify maximally independent spatial components (Calhoun et al., 2001. *A method for making group inferences from functional MRI data using independent component analysis*. Hum Brain Mapp 14, 140-151). This process then may be repeated 10 times in ICASSO and the best selection (most central) among these runs is used as the final solution (Ma et al., 2011. *Automatic identification of functional clusters in FMRI data using spatial dependence*. IEEE Trans Biomed Eng 58, 3406-3417). Finally, 50 of these components identified as being related to motion, imaging artifact or physiological processes were removed. The remaining 50 components were reported as the actual resting-state functional networks. These functional networks include auditory (AUD), visual (VIS), somatomotor (SM), cognitive control (CC), default mode (DM) and cerebellum (CB) networks. FIG. 8. Illustrates a visual depiction of these functional networks. GICA back-reconstruction then may be used to obtain subject-specific functional networks and corresponding time courses (TCs) from the group-level ICA and may include also processing of subject-specific TCs such as detrending, motion regression and outlier removal to reduce effects of noise (Erhardt et al., 2011. *Comparison of Multi-Subject ICA Methods for Analysis of fMRI Data*. Hum Brain Mapp 32, 2075-2095).

The subject-wise network time-courses may be analyzed using an embodiment of the invention to estimate dynamic functional network connectivity states derived from the dictionary elements of the decomposition. Input multivariate signal X may be formed as follows: for each row, we concatenate time-courses of a specific network for all subjects. This is repeated for each row, which corresponds to a different network. Consequently, the number of rows may be equal to the number of networks (50) and the number of columns may be equal to the number of subjects (405) multiplied by the number of timepoints in a time-course (148). FIG. 3A illustrates the application of one embodiment of the invention to actual rs-fMRI data. FIG. 3B illustrates five "dynamic connectivity states" derived from elements of dictionary D by self-cross product of each element. The number of dictionary elements, which also corresponds to number of derived connectivity states, may be selected based on elbow curve criteria (FIG. 9) that correspond to previous dynamic connectivity studies suggesting five "connectivity states" may describe most of the dynamics of the human brain during rest.

Figure 4:
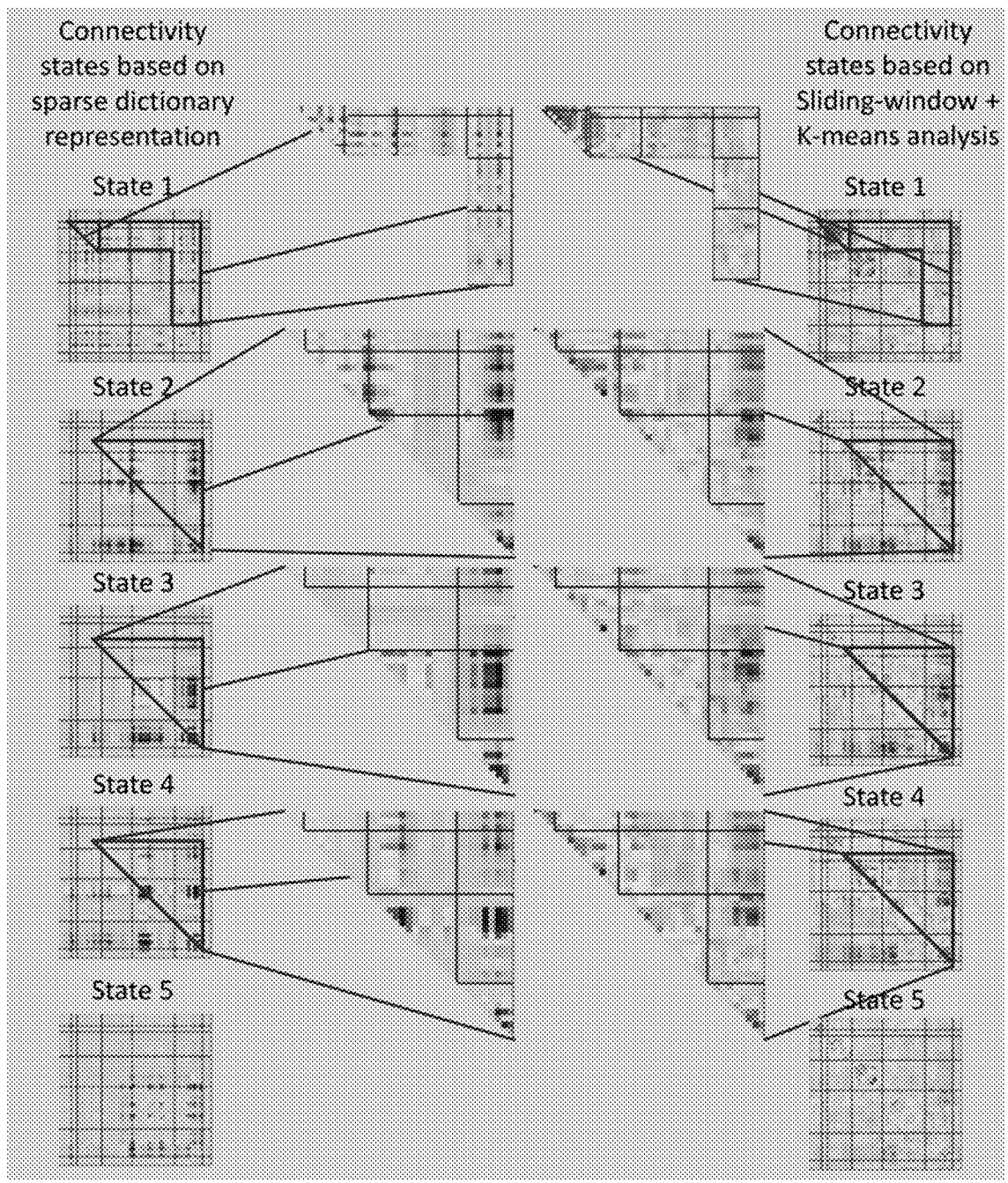
FIG. 4 illustrates a side-by-side comparison of the dynamic connectivity states estimated by one embodiment of the invention (left) and connectivity states estimated by sliding-window analysis (right). Connectivity states on the left have sharper modularity. The apparent similarities between the first two states of each approach decreases between the corresponding states three and four although each state still retain some visible connectivity patterns. The fifth state of each approach exhibits minimum similarity to any other states of the other approach. The fifth state—according to embodiments of the invention—displays a unique and more focal modularity constituting cognitive control and default mode regions whereas the windowed approach displays a much weaker and more diffuse connectivity pattern.

FIG. 4 illustrates a comparison of the connectivity states of networks of the brain captured through the use of an embodiment of the invention (left) and by the sliding-window approach (right). As is evident, the connectivity states 1 and 2 estimated according to an embodiment of the present invention display similar patterns to the corresponding connectivity states estimated by sliding window analysis. The similarity between the states of each method decreases in states 3 and 4 although there are still shared patterns of connectivity between corresponding states of each method. These similarities include connectivity patterns between default mode and visual networks as well as default modes and cognitive control networks in both state 3 and state 4 that may be shared between the corresponding states of both methods. Moreover, state 3 of both methods shares a similar in-between connectivity of cognitive control networks.

Further, at least one connectivity state for each method (e.g., the fifth state of each set) may be minimally correlated to any of the connectivity states in the other approach. The fifth state of the sliding-window analysis shows global weak connectivity between the majority of networks with very little visible modularity in connectivity pattern. However, in view of the limiting assumptions of the sliding-window analysis discussed above, it is not known what the actual connectivity of this state represents. It may represent connectivity with overall weak dependence between the majority of networks. However, it may represent also connectivity with significant dependence between the subset of networks, but due to the more spontaneous nature and a lower rate of occurrence, may not have been captured by the selected window. As such, it would likely be averaged with other unrelated connectivities also occurring in the same window, leading to an estimation of overall weak connectivity. Also, choosing the window length may be a crucial parameter of sliding-window approaches that may control the observable rates of change in the underlying dynamics. A large window means that samples belonging to unrelated dynamic connectivities may lie in the same window and may result in an incorrect estimation of connectivity corresponding to that window. On the other hand, a small window size may lead also to an incorrect estimation of dynamic connectivity due to an insufficient number of samples in the given window.

These findings highlight a major limitation of a sliding-window analysis for estimating the more transient states. In contrast, embodiments of the present invention do not include such limitations. In fact, all the states on the left show very specific and strong modularity in their corresponding patterns of connectivity. This may be a direct result of eliminating the need for a temporal smoothing operation that may blur spontaneous connectivity. As detailed further below, a simulation was conducted on a multivariate signal with a known dynamic covariance matrix to compare performance of embodiments of the present invention and the sliding-window approach in capturing ground truth dynamic covariance matrices that support the results described herein.

Figure 5:
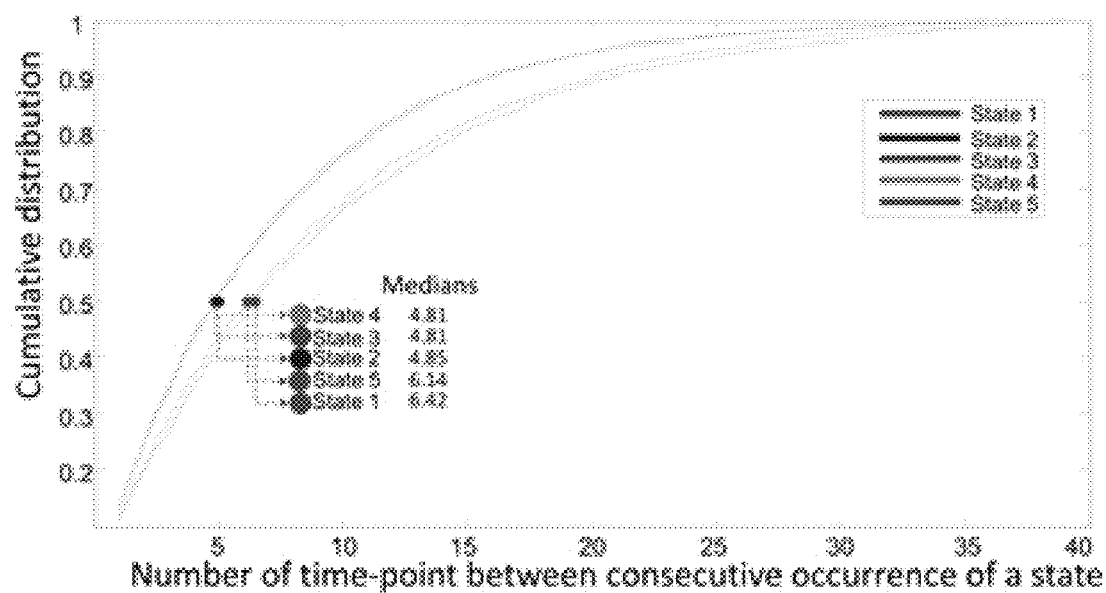
FIG. 5 illustrates a comparison of the cumulative distribution function of a number of time-points taken for consecutive occurrence of each connectivity state. If a connectivity state includes a longer period of time to reappear, it may mean that the connectivity state occurs less frequently and may be more spontaneous. Such a characteristic may not fit the locality assumption. As expected, state 5—which may be observable only through the use of an embodiment of the invention—displays a higher median of this measure compared to other connectivity states.

These observations prompted a measurement of the tendency of each state to be spontaneous. Accordingly, for each state, the number of timepoints between each consecutive occurrence of a given state was recorded as well as the median of the distribution of these measurements for each state. Less spontaneous states may show a smaller median for this distribution compared to a state that occurs more spontaneously. FIG. 5 illustrates the cumulative distribution function (CDF) of the above measurements for each state. The x-axis of the center of mass of this distribution corresponds to the median of the measure. As expected, state 5, followed by state 1, have a higher median compared to the other states.

The tendency of the connectivity states to be spontaneous provides insight into the underlying behavior of human dynamic connectivity during the resting state. For example, the number of data-points that has been assigned to each state varies between subjects and may be strongly correlated to the age and gender of subjects. However, measurements of this quantity, which may be referred to as the sample-density of each state, may only count assigned data-points that are also reasonably far from other states. And as explained above, these states may correspond to dominant linear patterns in the sample space that all intersect at the origin of this space. Consequently, data-points close to this intersection point are relatively close to other states. In order to have enough confidence in the assignment of the points, a sphere may be defined with radius 0.01 after z-scoring distances of all points from the origin (note that due to curse of dimensionality, the sphere does not need to be large) and exclude all the timepoints lying in this sphere for the desired measurement.

Next, a 5-dimensional (5-D) response variable may be formed of a number of assigned data-points to each state for each subject. Such variables may include gender (coded as 0: male, 1: female), log of age, and motion parameters as explanatory variables. An MANCOVA analysis (Allen et al., 2011. *A baseline for the multivariate comparison of resting-state networks*. Front Syst Neurosci 5, 2) may then be performed for the model selection using backward selection where gender is set as the factor log of age and motion parameters as covariates. Backward selection may reduce the explanatory variable only to gender and log(age) covariates followed by a linear regression analysis of each state's sample-density with gender and log(age) after regressing out the other variable. This analysis shows a significantly higher sample-density for state 4 (P-value 0.0004) in females than males. Moreover, states 1, 2, and 5 have lower sample-density as the age of the subjects increases (p-values 0.003, 0.0000 and 0.05 respectively).

To better understand the context of these studies, it may be helpful to first describe two natural but different generation models of a multivariate signal with a dynamic covariance. In the first model, it may be assumed that there is an underlying multivariate Gaussian distribution that may generate samples of the multivariate signal at each timepoint. This multivariate Gaussian distribution slowly changes into another Gaussian distribution with a different covariance. As explained above, this may be a perfect model for analyses— based on a sliding-window format—since with the right choice of the window size, the slow varying covariance may be estimated at each timepoint. In the second model, it may be assumed that a fixed number of multivariate Gaussian distributions—each with different covariance matrices— may determine randomly the distribution from which the sample at the current timepoint is taken. This sampling may be repeated at each timepoint in order to generate the multivariate signal. FIG. 1A and FIG. 1B illustrate the differences between the two models. Based on the first model with different distribution at different periods of time, the sliding-window may capture the true underlying dynamic dependence in the form of correlation matrix (FIG. 1A). Importantly, there may be also instances in which samples belonging to different distributions lie in the same window and may lead to an inaccurate and non-existing estimation of dependence. For the second model, there is no assumed knowledge about which distribution occurs at each timepoint and, consequently, any estimation from the samples makes no assumptions regarding when the states occur. FIG. 1B illustrates the samples shown jointly in the corresponding sample space. As is evident, the use of embodiments of the present invention may capture the underlying dynamic covariances from these samples in the form of "dictionary elements" even in the absence of temporal dimension. Moreover, the dictionary elements may translate into the "lines" as the representation of the dominant linear patterns in this sample space. Conversely, the sliding-window approach (or any other approaches that require a smoothing operation in the temporal domain) may be unable to capture the underlying dynamic dependence from these time-less samples.

Figure 6A:
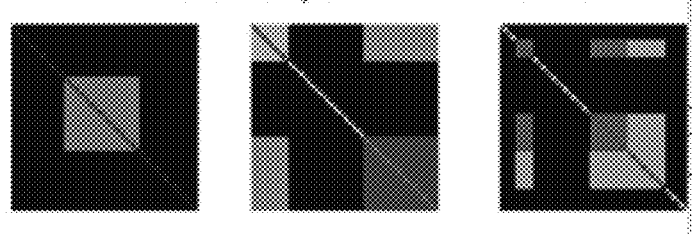
FIG. 6A illustrates the results of the use of one embodiment of the invention to capture ground-truth underlying dynamic coherence of a multivariate signal as compared to sliding-window approach represented by Ground-truth dynamic coherence matrices of the signal.
Figure 6B:
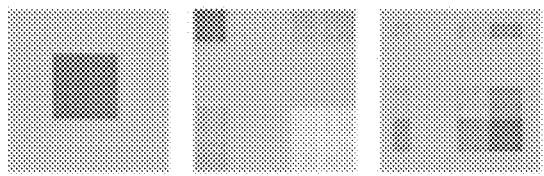
FIG. 6B illustrates a side-by-side result of an analysis of connectivity states using one embodiment of the invention (left) and sliding-window approach (right) when the simulation is based on locality assumption.
Figure 6B:
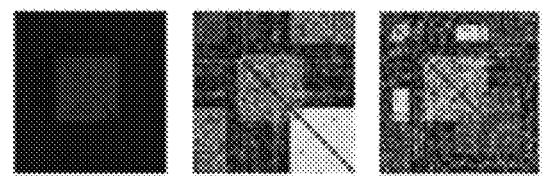
Figure 6C:
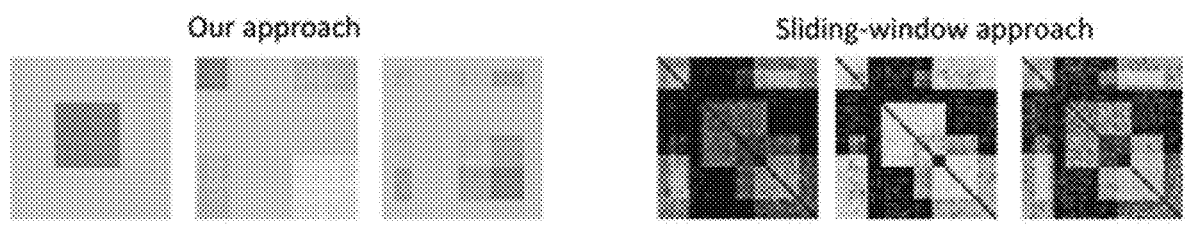
FIG. 6C illustrates the same results when data-points of the signal are randomly permuted in time, which corresponds to a heterogeneous rate of changes of dynamic coherence that does not follow locality assumption.
Figure 6D:
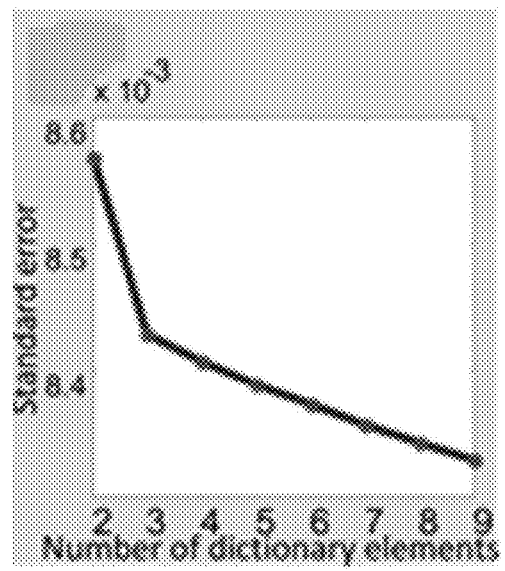
FIG. 6D illustrates a selected number of dynamic covariance states based on the elbow-curve analysis.

FIG. 6A illustrates a simulation based on these two models in order to study and compare performance of embodiments of the present invention to a sliding-window analysis. This simulation may include the steps of defining three separate 50×50 covariance matrices each with a unique modularity are defined; randomly choosing one of these matrices and set it as the covariance matrix of a multivariate Gaussian distribution function; deriving 49 samples from this PDF and set those as the 49 consecutive data-points of the desired simulated signal; repeating these steps 500 times and feeding the final simulated signal into K-SVD such that the signal may be decomposed into a dictionary matrix with three elements and the corresponding sparse mixing matrix. This corresponds to the first model of a signal with dynamic covariance matrix. FIG. 6B illustrates the self-cross product of each dictionary element that may correspond to each of the original dynamic covariance matrices. FIG. 6B illustrates also the results of sliding-window analysis to capturing the underlying connectivities. However, embodiments of the present invention are invariant to the random permutation of timepoints since these methods are estimating the covariance matrices in the sample space. Random permutation of the simulated signal may correspond to the second model of a signal with dynamic covariance, where, at each timepoint, a covariance matrix is randomly selected. FIG. 6C illustrates the result of the use of one embodiment of the invention on the simulated signal when the samples are randomly shuffled in time. The permutation causes the signal to have changes of covariance at a rate as high as one timepoint thus a permitting circumvention of the ground truth covariance matrices even on the permuted signal. As is shown at FIG. 6C, the sliding-window approach is unable to separate the underlying dynamic covariances because it is based on locality assumption.

In order to show that the latter model is not just a conceptual model and it, in fact, applies to natural and common systems, it may be useful to consider a popular system for resource allocation that is widely used in computation devices such as personal computers. In such systems, there are multiple processes sending request for shared resources. If a resource is allocated to a single process for a relatively long period of time, the lag is cascaded to other processes, eventually causing delays in the performance of the whole system. This is the main reason for the commonly used strategy to alternate the resource allocation at a higher rate so that all processes experience fairly similar lags given that the processes have the same priority.

And although the underlying cognitive processes of the brain may not necessarily follow the same model, if specific functional connectivity is considered as the necessary resource for a specific cognitive process in the brain, there may be a logical reason to believe that any smoothing assumption may be limited in capturing the underlying dynamic connectivity states. FIG. 4 suggests also a strong resemblance between the majority of the connectivity states captured by embodiments of the invention and a sliding-window analysis that supports the smoothing assumption and may show a connectivity pattern that is only captured by the inventive method that includes a strong correlation with gender.

Importantly, these studies indicate that the dynamic connectivity estimated from the resting-state brain has heterogeneous rates of change and, consequently, methods that do not address this property, may be unable to capture all the underling aspects of dynamic connectivities. Embodiments of the present invention do not have such limiting assumptions. That is to say, these embodiments may capture arbitrary rates of change of dynamic connectivities and the only limitation is the one imposed by the sampling rate itself (Nyquist rate).

There is also another approach known as Co-Activation Pattern (CAP) analysis that is not based on a locality assumption. However, CAP lacks an actual formulation for capturing dynamic linear dependence according to embodiments of the present invention.

Figure 7:
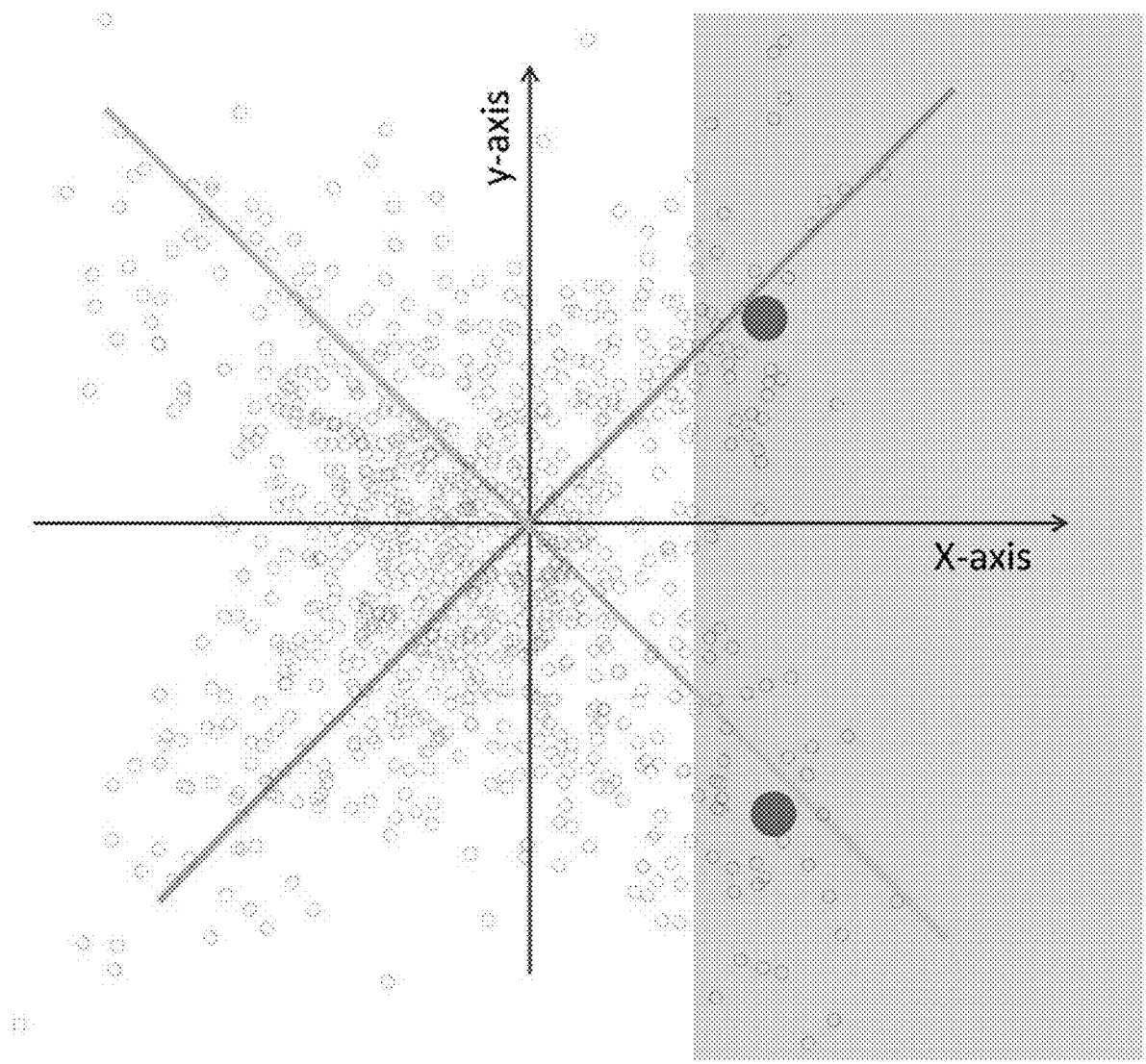
FIG. 7 illustrates a comparison of one embodiment of the invention and CAP analysis in which the sample space of an input 2-D signal is represented in a 2-D plane.

More specifically, the differences between CAP and the inventive methods may be better understood by examining what each method is looking for in the sample space. In the inventive method, dynamic covariance maps to multiple dominant linear patterns in the sample space by estimating these patterns. CAP analysis, on the other hand, is looking for the "activation status" of other dimensions of input multivariate signal (which in the original study constitutes ROI-level resting-state BOLD signal) when the selected dimension (selected seed) of the signal is activated. The activation is determined by a threshold value. FIG. 7 illustrates the concept of CAP analysis used to study the sample space. In CAP analysis, a 2-d signal includes samples that may be driven from two different Gaussian random processes. The covariance matrices of these random processes may be captured by the dominant linear patterns in the sample space. Then, CAP analysis selects a seed dimension (x-axis here). Next, a threshold value may be selected along that axis based on 90-percent quantile (thresholding is represented by a half space (gray box)). After thresholding, the analysis may be followed by a clustering of the samples which survive the threshold which are then k-means clustered with k=2. The centroids of the clusters represent the "co-activation patterns". As is evident, centers of the clusters are points in the sample space that are very close to the dominant linear patterns captured through the user of the inventive methods. However, mathematically speaking, we are unable to say anything about the actual underlying covariance matrices as when we are only given points and not the linear pattern itself which is provided by our method.

Figure 9:
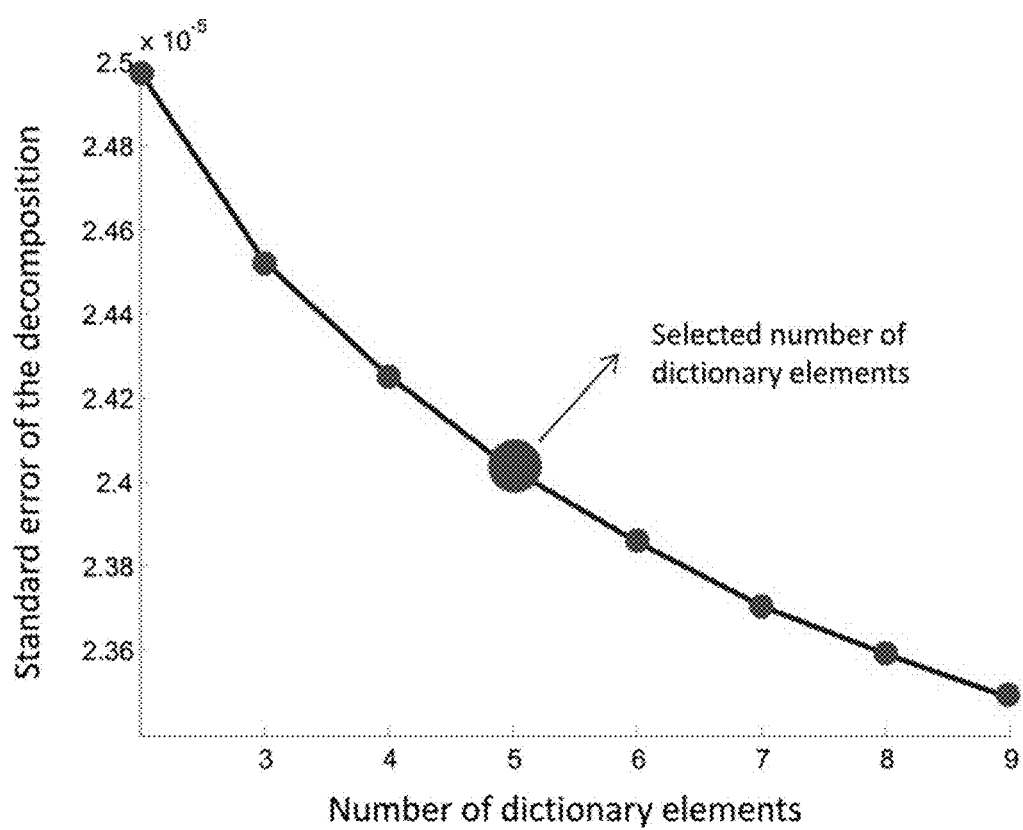
FIG. 9 illustrates a plot of estimated standard error of the test data decomposition given the trained dictionary. Based on elbow criteria, five dictionary elements are used throughout the analyses.

FIG. 9 illustrates a graphical plot of estimated standard error of the test-data decomposition given the trained dictionary, that is, a dictionary with five elements reasonably lies on the elbow of the plot and, consequently, may use this number throughout the analyses.

Figure 10:
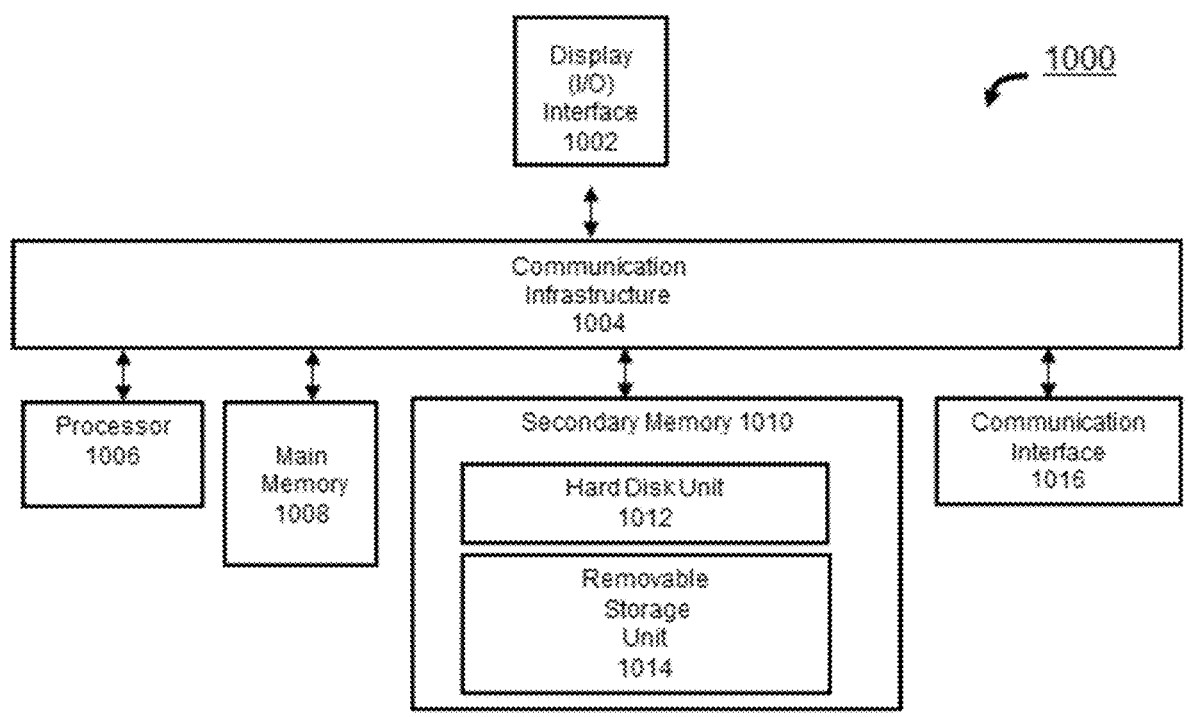
FIG. 10 illustrates an exemplary computer system for use with embodiments of the invention.

FIG. 10 illustrates an exemplary computer system 1000 that may be used to implement the methods according to the invention. One or more computer systems 800 may carry out the methods presented herein as computer code.

Computer system 1000 includes an input/output display interface 1002 connected to communication infrastructure 1004—such as a bus—which forwards data such as graphics, text, and information, from the communication infrastructure 1004 or from a frame buffer (not shown) to other components of the computer system 1000. The input/output display interface 1002 may be, for example, a keyboard, touch screen, joystick, trackball, mouse, monitor, speaker, printer, any other computer peripheral device, or any combination thereof, capable of entering and/or viewing data.

Computer system 1000 includes one or more processors 1006, which may be a special purpose or a general-purpose digital signal processor that processes certain information. Computer system 1000 also includes a main memory 1008, for example random access memory ("RAM"), read-only memory ("ROM"), mass storage device, or any combination of tangible, non-transitory memory. Computer system 1000 may also include a secondary memory 1010 such as a hard disk unit 1012, a removable storage unit 1014, or any combination of tangible, non-transitory memory. Computer system 1000 may also include a communication interface 1016, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 1008, secondary memory 1010, communication interface 1016, or a combination thereof, function as a computer usable storage medium, otherwise referred to as a computer readable storage medium, to store and/or access computer software including computer instructions. For example, computer programs or other instructions may be loaded into the computer system 1000 such as through a removable storage device, for example, a floppy disk, ZIP disks, magnetic tape, portable flash drive, optical disk such as a CD or DVD or Blu-ray, Micro-Electro-Mechanical Systems ("MEMS"), nanotechnological apparatus. Specifically, computer software including computer instructions may be transferred from the removable storage unit 1014 or hard disc unit 1012 to the secondary memory 1010 or through the communication infrastructure 1004 to the main memory 1008 of the computer system 1000.

Communication interface 1016 allows software, instructions and data to be transferred between the computer system 1000 and external devices or external networks. Software, instructions, and/or data transferred by the communication interface 1016 are typically in the form of signals that may be electronic, electromagnetic, optical, or other signals capable of being sent and received by the communication interface 1016. Signals may be sent and received using wire or cable, fiber optics, a phone line, a cellular phone link, a Radio Frequency ("RF") link, wireless link, or other communication channels.

Computer programs, when executed, enable the computer system 1000, particularly the processor 1006, to implement the methods of the invention according to computer software including instructions.

The computer system 1000 described herein may perform any one of, or any combination of, the steps of any of the methods presented herein. It is also contemplated that the methods according to the invention may be performed automatically or may be invoked by some form of manual intervention.

The computer system 1000 of FIG. 10 is provided only for purposes of illustration, such that the invention is not limited to this specific embodiment. It is appreciated that a person skilled in the relevant art knows how to program and implement the invention using any computer system.

The computer system 1000 may be a handheld device and include any small-sized computer device including, for example, a personal digital assistant ("PDA"), smart handheld computing device, cellular telephone, or a laptop or netbook computer, hand held console or MP3 player, tablet, or similar hand held computer device, such as an iPad®, iPad Touch® or iPhone®.

Embodiments of the invention may be also directed to computer products, otherwise referred to as computer program products. Computer products store software on any computer useable medium, known now or in the future. Such software, when executed, may implement the methods according to certain embodiments of the invention.

Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for capturing dynamic covariance of a multivariate signal comprising the steps of:
   receiving an input multivariate signal;
   decomposing the input multivariate signal into a dictionary and a sparse mixing matrix, wherein the decomposing step further comprises the step of representing the input multivariate signal as a plurality of data points, wherein each data point is represented by a singleton dictionary element; and
   estimating the dynamic covariance of a partition of datapoints using a self-outer product, wherein the self-outer product corresponds to the singleton dictionary element up to a scaling value.

2. The method of claim 1, wherein the method does not require a locality assumption.

3. The method of claim 1, wherein the dictionary is defined according to:

$$\min_{D,M} \|X(t) - M(t)D\|_2 + \lambda \sum_i \|[m_{1...k}(i)]\|_0$$

wherein X(t) is an input matrix with dictionary $D \in \mathbb{R}^{k \times n}$ and mixing matrix $M(t) = [m_1(t), m_2(t), \ldots, m_k(t)] \in \mathbb{R}^{T \times k}$ where k is a number of dictionary elements, and $m_{1\ldots k}(i)$ is an ith row of the mixing matrix M and $\lambda$ is a regularizer parameter controlling a degree of sparsity.

4. The method of claim 3, wherein a row of the X(t) is a sparse linear combination of the dictionary D of rows of the mixing matrix M(t).

5. The method of claim 3, further comprising calculating the dynamic covariance according to the following equation:

$$\min_{D,M(t)} \|X(t) - M(t)D\|_2 \text{ s.t. } \forall i \ \|m_{1\ldots k}(i)\|_0 = 1$$

wherein $\|m_{1\ldots k}(i)\|_0 = 1$ is a hard constraint.

6. The method of claim 1, further comprising calculating a rank-1 estimate of the input multivariate signal according to the following:

$$X(t) \cong m(t)v^T$$

7. The method of claim 1, further comprising finding disjoint partitions $s_i$ of the input multivariate signal according to the following:

$$\sum_{i=1}^{k} C_i$$

where $C_i = \|X(t) - m(t) v_i^T\|_2$ and $t \in s_i$.

* * * * *

UNITED STATES PATENT AND TRADEMARK OFFICE
CERTIFICATE OF CORRECTION

PATENT NO. : 11,402,452 B2
APPLICATION NO. : 16/198446
DATED : August 2, 2022
INVENTOR(S) : Maziar Yaesoubi and Vince Calhoun It is certified that error appears in the above-identified patent and that said Letters Patent is hereby corrected as shown below:

On the Title Page

Item (71), under Applicant, delete "STC.UNM" and insert -- UNM Rainforest Innovations --

Signed and Sealed this
Twenty-seventh Day of December, 2022

Katherine Kelly Vidal
*Director of the United States Patent and Trademark Office*